US010704543B2

(12) United States Patent
Bode et al.

(10) Patent No.: US 10,704,543 B2
(45) Date of Patent: Jul. 7, 2020

(54) DISTRIBUTOR HEAD FOR A SUCTION PUMP

(71) Applicant: SARTORIUS LAB INSTRUMENTS GMBH & CO. KG, Goettingen (DE)

(72) Inventors: Jonas Bode, Uslar (DE); Malte Staender, Heiligenstadt (DE)

(73) Assignee: SARTORIUS LAB INSTRUMENTS GMBH & CO., KG, Goettingen (DE)

( * ) Notice: Subject to any disclaimer, the term of this patent is extended or adjusted under 35 U.S.C. 154(b) by 0 days.

(21) Appl. No.: 16/366,258

(22) Filed: Mar. 27, 2019

(65) Prior Publication Data

US 2019/0219045 A1    Jul. 18, 2019

Related U.S. Application Data

(63) Continuation of application No. PCT/EP2017/000848, filed on Jul. 14, 2017.

(30) Foreign Application Priority Data

Sep. 27, 2016  (DE) .................. 10 2016 118 183

(51) Int. Cl.
| | |
|---|---|
| *F04B 39/08* | (2006.01) |
| *A61M 5/14* | (2006.01) |
| *G01G 17/04* | (2006.01) |
| *F04B 39/10* | (2006.01) |
| *G01N 35/08* | (2006.01) |

(52) U.S. Cl.
CPC ........... *F04B 39/08* (2013.01); *A61M 5/1408* (2013.01); *F04B 39/10* (2013.01); *G01G 17/04* (2013.01); *G01N 35/085* (2013.01)

(58) Field of Classification Search
CPC ....... G01N 35/085; F04B 39/08; F04B 39/10; Y10T 137/87877
USPC ......................................... 137/883
See application file for complete search history.

(56) References Cited

U.S. PATENT DOCUMENTS

| | | | | | |
|---|---|---|---|---|---|
| 5,915,414 | A | * | 6/1999 | Seaman | ............ H01L 21/67017 137/377 |
| 6,637,476 | B2 | * | 10/2003 | Massaro | ............ G01N 35/0099 141/1 |
| 7,644,725 | B2 | * | 1/2010 | Matsuzawa | ............. F16K 11/22 137/240 |

FOREIGN PATENT DOCUMENTS

| | | |
|---|---|---|
| EP | 2759816 B1 | 1/2016 |
| WO | 8800347 A1 | 1/1988 |

OTHER PUBLICATIONS

International Search Report, PCT/EP2017/000848, dated Sep. 13, 2017, 4 pages.

(Continued)

*Primary Examiner* — Michael R Reid
(74) *Attorney, Agent, or Firm* — Edell, Shapiro & Finnan, LLC

(57) ABSTRACT

A distributor head for a suction pump which includes a housing (12), a pump port (16) configured to apply a negative pressure, and a plurality of hollow needles (18). The hollow needles are fixed to the housing (12), are connected in a liquid-tight manner to the pump port (16), and are arranged parallel to and at a distance from one another. Individual connecting paths (34) of the hollow needles (18) to the pump port (16) include respective, independently operable control valves (36).

6 Claims, 2 Drawing Sheets

(56) References Cited

OTHER PUBLICATIONS

PCT International Preliminary Report, PCT/EP2017/000848, dated Jun. 29, 2018, 5 pages.

* cited by examiner

DISTRIBUTOR HEAD FOR A SUCTION PUMP

CROSS REFERENCE TO RELATED APPLICATIONS

This is a Continuation of International Application PCT/EP2017/000848, which has an international filing date of Jul. 14, 2017, and which claims the priority of German Patent Application 10 2016 118 183.8, filed Sep. 27, 2016. The disclosures of both applications are incorporated in their respective entireties into the present Continuation by reference.

FIELD OF THE INVENTION

The invention relates to a distributor head for a suction pump, comprising
a housing,
a pump port for applying a negative pressure and
a plurality of hollow needles, which are fixed to the housing, are connected in a liquid tight manner to the pump port, and are arranged parallel to and at a distance from one another.

BACKGROUND

A test apparatus for gravimetric testing of multi-channel pipettes is known from the published document EP 2 759 816 B1. Such test apparatuses contain a plurality of load cells that are offset from one another in a housing. The load receptors of said load cells are arranged equidistant in a straight, horizontal row. Each load receptor carries a narrow, cylindrical vessel, into which liquid can be pipetted from a pipette during the test procedure. The arrangement of the individual load receptors and their pipetting vessels is adapted to the arrangement of the pipette tips of the multi-channel pipette to be calibrated. In this way, all of the pipette channels can be emptied simultaneously into the respectively assigned pipetting vessels; and the respective pipetting volume can be determined gravimetrically. Before each new pipetting process, the load cells can be tared as needed, so that the respective pre-fill level of the vessels does not affect the individual measurements. However, after a certain number of test procedures, it is absolutely necessary to empty the pipetting vessels. For this purpose the cited published document discloses the parallel emptying of all of the pipetting vessels by suction using a multi-channel suction pump.

Such suction pumps typically comprise a single pumping station, which generates the necessary negative pressure and which is connected to the pump port of a distributor head conforming to its genre. The distributor head comprises a plurality of hollow needles, which are fixed to the housing of the distributor head; and said distributor head has an arrangement and orientation that are adapted to those of the pipetting vessels of the gravimetric test apparatus. The individual hollow needles are connected in a liquid tight manner to the pump port. For this purpose there is usually a main line that is connected to the pump port, from which individual branch lines diverge to the individual hollow needles. Of course, it is also possible to route the individual line from each hollow needle to the common pump port. For the pumping out operation, the distributor head is positioned in such a way that all of the hollow needles are immersed in the pipetting vessels as far as to the desired immersion depth. Then the negative pressure, generated by the pumping station, is distributed to all of the suction channels, so that the liquid is aspirated from all of the pipetting vessels in parallel.

However, problems may arise, if the fill level in one pipetting vessel is significantly lower than in another pipetting vessel. The vessel that is only slightly filled will soon be sucked dry, so that the corresponding hollow needle draws air. If an extremely strong and, thus, large, heavy and expensive pumping station is not used, the result will be a disruption in the liquid column in the common line area, so that the aspiration will stop altogether. Therefore, vessels that are filled to a higher level will not be completely aspirated. If, however, it is falsely assumed, as the pipetting procedure continues, that all of the vessels are empty, then the vessels may overflow and cause damage to the sensitive inner structure of the test apparatus.

SUMMARY

One object of the present invention is to further develop a generic distributor head for suction pumps in such a way that a reliably uniform aspiration on all channels is ensured.

According to one formulation of the invention, this object is achieved in that the individual connecting paths of the hollow needles to the pump port have in each case an independently operable control valve. Preferred embodiments of the invention are the subject matter of the dependent patent claims.

Due to the control valve, which is associated with each individual channel and which in each case has to be arranged, of course, in the channel-specific section of the respective connecting path, it is possible to block the individual channels individually and independently of one another. If, thus, one of the pipetting vessels is emptied prematurely, and consequently its associated hollow needle draws air, then the corresponding suction channel can be closed, so that the negative pressure, generated by the pumping station, is distributed only to the remaining, open channels, so that consequently the vessels, associated with said open channels, continue to be emptied by aspiration. Thus, by successively shutting off each air-drawing channel, the uniform emptying of all of the vessels, i.e., their emptying to the same residual fill level (which, of course, also includes suction until completely empty), can be ensured.

In this context it can be provided, as in the case of a preferred embodiment of the invention, that the hollow needles are individually adjustable in their vertical position. As a result, it is possible to achieve an adaptation to possibly different vertical positions of the pipetting vessels inside the test apparatus. Thus, it is also possible to specify different residual fill levels for different pipetting vessels.

In order to facilitate the detection of an air-drawing channel and, thus, its targeted shutoff, it is provided in a further development of the invention that each control valve is assigned a test chamber, the inner space of which is part of the respective connecting path, and the outer wall of which includes a viewing window that penetrates the housing. As soon as a channel draws air, bubbles appear in said channel; and these bubbles migrate in the direction of the pumping station. In so doing, they also pass through the test chamber, a feature that can be detected by the user through the viewing window from the outside. Due to the predetermined assignment of each viewing window to a specific control valve, it is easy to identify the control valve that is to be switched in order to shut off the channel.

The test chambers are preferably arranged on the hollow needle side of the respective associated control valve in the respective connecting path. It has been found, in particular, that the control valves act—at least in the closed state—as insulators for the rapid pressure fluctuations, which propagate in the connecting paths and are generated by the pumping station. These pressure fluctuations cause the air bubbles in the test chamber to tremble, which can be seen through the viewing window. Therefore, as a result of the hollow needle-sided arrangement of the test chambers, it is possible to clearly distinguish through the resting or trembling of the air bubble a channel with (after air drawing) an already closed valve from a channel with an open valve.

As an alternative to the above described visual detection of bubbles and the manual shutoff of the individual channels by a human user, an automation is also possible as an alternative. The person skilled in the art in question is aware of a variety of methods for bubble detection, for example, optically or capacitively. These measures can be easily coupled to an electronic control of the valves.

At the beginning of each aspiration process, all of the valves should be open. Only in this way can it be ensured that all of the vessels are aspirated. If a valve that was closed individually during a previous aspiration process remains inadvertently closed during the next aspiration process, then an unwanted overflow may occur during subsequent pipetting operations. In the context of the aforementioned, electronics-based automation, it is not a problem to ensure this with programming technology. In order to also make embodiments, which are operated strictly by hand, not prone to errors, it is provided in a further development of the invention that the control valves are designed as normally open valves that are sensitive to negative pressure. A normally open valve is generally referred to by the person skilled in the art in question as a valve that is open in the non-actuated state. In this case "non-actuated" can denote not only a non-existent mechanical actuation, but also the absence of current flow to an electric valve. The term "sensitive to negative pressure" means in this context that the non-actuated state, i.e., open state, of the valve occurs automatically, if no negative pressure is applied to the valve. The skilled person knows various ways of implementing this in the case of both electrical and also strictly mechanical valves.

The insertion of the parallel hollow needles into the pipetting vessels has to be done carefully in order to prevent the needles from impinging on the vessel wall and, in so doing, possibly damaging the load cells. Therefore, it is provided in a further development of the invention that the distributor head is guided moveably with at least one telescopic rod that is arranged parallel to the hollow needles on the housing. The telescopic rod can be placed directly or indirectly on the pipette test apparatus, so that the movement of the distributor head is carried out in a guided manner when the hollow needles are lowered into the pipetting vessels. In this case the telescopic rod can be used only to guide the movement. However, it is also conceivable that a motorized traversibility is implemented with a drive that is integrated in the telescopic rod, for example, a spindle drive. In order to also prevent rotation about the telescopic rod, preferably two or more telescopic rods are provided to guide the movement. These telescopic rods can be placed directly on the test apparatus or, preferably, can be connected through a frame plate, which in turn can be placed in a positionally accurate manner on the test apparatus. The positional accuracy can be ensured, in particular, with corresponding form-fitting contours on the frame plate and the test apparatus.

The residual fill level to be reached following aspiration may vary as a function of the specific application. In particular, complete aspiration can be provided, if no further test passes are intended. However, different test standards specify a minimum fill level of the pipetting vessels during the test pipetting process. In order to meet such different requirements, it is provided in a further development of the invention that the distributor head comprises an adjustable stop that limits its travel path. It is particularly preferred that this stop be integrated in the telescopic rod.

In order to avoid shocks, the telescopic rod is conveniently provided with a damping mechanism. In this case said damping mechanism may be a hydraulic damper, as known, for example, from industrial shock absorbers. This allows a jerkless retraction of the distributor head into its aspirating position.

As an alternative or in addition to a telescopic rod, it is also possible to use, as a matter of fact, a rigid guide rod.

Other features and advantages of the invention will become apparent from the following specific description and the drawings.

DETAILED DESCRIPTION

Figure 1:
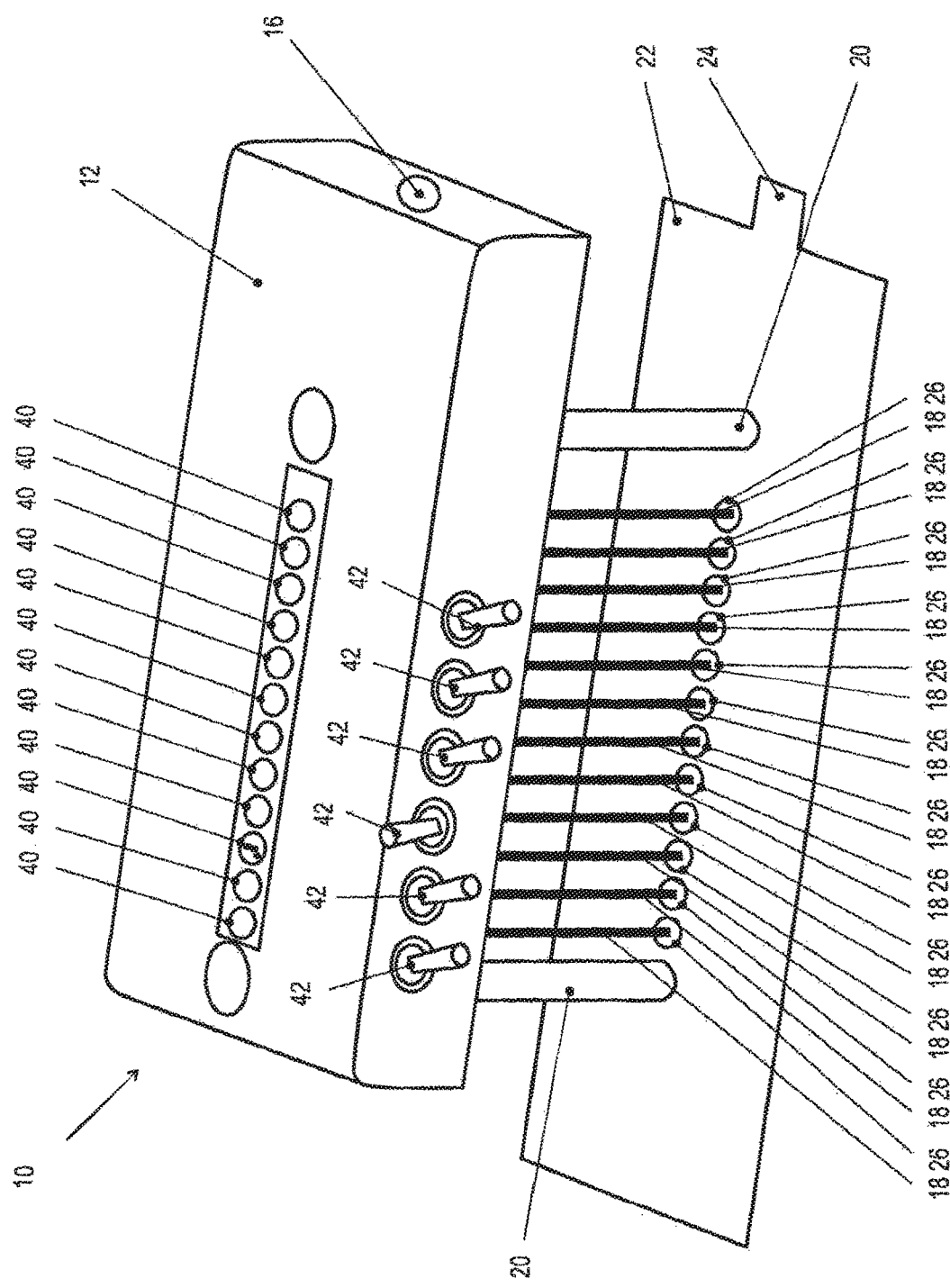
FIG. 1: a simplified perspective view of a distributor head in accordance with the present invention

Identical reference numerals in the figures indicate the same or analogous elements.

FIG. 1 shows a simplified, perspective view of a preferred embodiment of a distributor head 10 in accordance with the invention. The distributor head 10 comprises a housing 12, in which a line arrangement 14 is provided, as shown in the schematic representation in FIG. 2. The line arrangement 14 connects a pump port 16 to a plurality of hollow needles 18 inside the housing. In the illustrated embodiment twelve hollow needles are provided; however, the concrete number of these hollow needles is not essential to the invention. The hollow needles 18 are aligned parallel to each other and are fixed to the housing 12 in a straight, equidistant row.

The housing is connected via two telescopic rods 20 to a positioning plate 22, which can be positioned exactly on a gravimetric test apparatus (not shown) for multi-channel pipettes. In this case the positional accuracy is ensured through form fitting contours 24 that find corresponding contours on the test apparatus. The positioning of the positioning plate 22 on the test apparatus is carried out in such a way that the hollow needles 18 are positioned exactly above the pipetting vessels that are to be aspirated. By compression of the telescopic rods 20, the hollow needles 18 can be lowered vertically and without contact into the pipetting vessels, so that they pass through the corresponding breakthroughs 26 in the positioning plate 22. At the same time the immersion depth can be adjusted with an adjustable stop, which is not shown in detail in FIG. 1.

The pump port 16 serves to connect in a liquid tight manner a pumping station 28, with which a negative pressure can be generated, so that liquid can be aspirated from the pipetting vessels through the hollow needles 18 and the line arrangement 14 into a tank 30.

Figure 2:
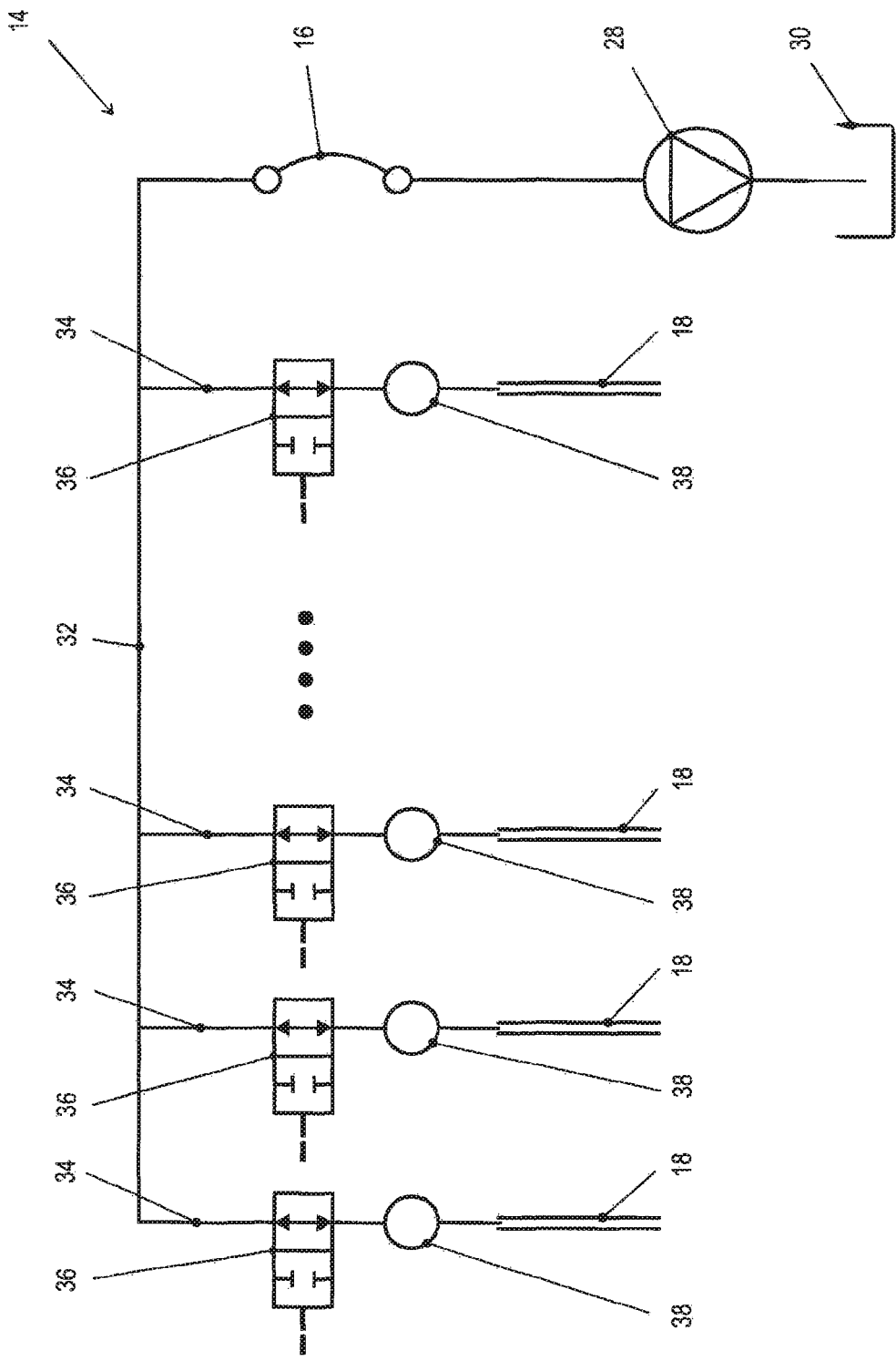
FIG. 2: a schematic representation of the arrangement of the lines in the distributor head from FIG. 1.

As can be seen in FIG. 2, the line arrangement 14 comprises a main line 32, from which a branch line 34 diverges for each hollow needle 18. The branch lines 34 pass in each case through a control valve 36, which is designed as a normally open valve that is sensitive to negative pressure, and open into the hollow needles 18. On the hollow needle side of the control valves 36, a test chamber 38 is arranged in each branch line 34; and a chamber wall of the test chamber is formed as a viewing window 40 in the lid of the housing 12.

After the hollow needles 18 have been positioned in the pipetting vessels to be aspirated, the pumping station 28 is switched on. Liquid is pumped from the pipetting vessels into the tank 30 through the open valves 36. If in this case the liquid level in one pipetting device drops below the free end of the associated hollow needle 18, then this hollow needle draws air. Correspondingly bubbles form in the test chamber 38, and these bubbles can be detected through the corresponding viewing window 40 for the user. In FIG. 1, such bubbles are shown in the third window from the left. In order to enable further aspiration of the other pipetting vessels, the corresponding branch line 34 can be blocked with a respective switch 42 that is assigned to each control valve 36. Then the line system 14 no longer draws any air at all, so that liquid can still be aspirated from the pipetting vessels until the liquid level of another vessel drops below the tip of the associated hollow needle 18. In the embodiment shown in FIG. 1, the third switch 42 from the left is assigned to the test chamber 38, which is visible through the third viewing window 40 from the left; and this third switch is shown in the already actuated position. In the illustrated embodiment the six visible switches 42 are assigned to the six hollow needles 18 on the left, whereas the control valves 34, which are assigned to the six hollow needles 18 on the right, are actuated with switches on the invisible, opposite side of the housing.

The embodiments that are discussed in the specific description and shown in the figures represent exemplary embodiments of the present invention that are shown merely for illustrative purposes. The person skilled in the art in question is given, in light of the disclosure herein, a wide range of possible variations. In particular, an automation of the aspiration process explained above is possible, wherein both the switching of the valves and also the bubble detection can be automated individually or collectively. Although the distributor head of the present invention has been described herein as a separate module predominantly in the context of an exemplary embodiment, the invention also extends to embodiments in which the distributor head is an integral part of a more complex arrangement.

LIST OF REFERENCE NUMERALS

10 distributor head
12 housing
14 line arrangement
16 pump port
18 hollow needle
20 telescopic rod
22 positioning plate
24 form fitting contour
26 breakthrough in 22
28 pumping station
30 tank
32 main line
34 branch line
36 control valve
38 test chamber
40 viewing window
42 switch

What is claimed is:

1. Distributor head for a suction pump, comprising
   a housing,
   a pump port configured to apply a negative pressure and
   a plurality of hollow needles, which are fixed to the housing, are connected in a liquid-tight manner to the pump port, and are arranged parallel to and at respective distances from one another,
   wherein the plurality of hollow needles have respective individual connecting paths to the pump port that each comprise respective control valves that are operable independently from one another, wherein each of the control valves is assigned a respective test chamber, respective inner spaces of the chambers are part of the respective connecting paths, and an outer wall of the chambers comprises a viewing window penetrating the housing, and
   wherein the test chambers are arranged on hollow needle sides of the respective control valves in the respective connecting paths.

2. Distributor head, as claimed in claim 1, wherein the plurality of hollow needles are each individually adjustable in a vertical position.

3. Distributor head, as claimed in claim 1, wherein the control valves are negative pressure-sensitive normally open valves.

4. Distributor head, as claimed in claim 1, further comprising at least one telescopic rod arranged parallel to the hollow needles on the housing and configured to moveably guide the housing relative to an exterior plate.

5. Distributor head, as claimed in claim 4, further comprising an adjustable stop limiting a travel path of the housing relative to the plate.

6. Distributor head, as claimed in claim 4, wherein the telescopic rod comprises a damping mechanism.

* * * * *